United States Patent [19]

Viera et al.

[11] Patent Number: 5,267,574
[45] Date of Patent: Dec. 7, 1993

[54] GUIDEWIRE WITH SPRING AND A HEAT SHRINKABLE CONNECTION

[75] Inventors: Fernando M. Viera, Hialeah; Philip P. Corso, Jr., Davie, both of Fla.

[73] Assignee: Cordis Corporation, Miami Lakes, Fla.

[21] Appl. No.: 942,777

[22] Filed: Sep. 10, 1992

[51] Int. Cl.⁵ ............................................. A61B 6/00
[52] U.S. Cl. ..................................... 128/772; 604/164; 604/280
[58] Field of Search .............. 128/772, 657; 604/95, 604/164, 280, 282, 96

[56] References Cited

U.S. PATENT DOCUMENTS

| | | | |
|---|---|---|---|
| 3,906,938 | 9/1975 | Fleischhacker | 128/772 |
| 4,456,017 | 6/1984 | Miles | 128/772 |
| 4,538,622 | 9/1985 | Samson et al. | |
| 4,545,390 | 10/1985 | Leary | |
| 4,724,846 | 2/1988 | Evans, III | |
| 4,757,827 | 7/1988 | Buchbinder | 128/772 |
| 4,846,186 | 7/1989 | Box et al. | 128/657 |
| 4,922,924 | 5/1990 | Gambale et al. | |
| 5,059,183 | 10/1991 | Semrad | 604/158 |
| 5,063,935 | 11/1991 | Gambale | 128/657 |
| 5,069,226 | 12/1991 | Yamauchi et al. | 128/772 |
| 5,105,818 | 4/1992 | Christian et al. | 128/662.06 |
| 5,122,136 | 6/1992 | Guglielmi et al. | 606/32 |
| 5,135,503 | 8/1992 | Abrams | 604/164 |
| 5,141,494 | 8/1992 | Danforth et al. | 604/96 |
| 5,147,317 | 9/1992 | Shank et al. | 604/164 |

*Primary Examiner*—Stephen C. Pellegrino
*Assistant Examiner*—Guy V. Tucker
*Attorney, Agent, or Firm*—Watts, Hoffmann, Fisher & Heinke Co.

[57] ABSTRACT

A guidewire having a high radiopacity at the guidewire's distal tip. A spring mounted to the guidewire has one uniform diameter coiled region and a second tapered region. The tapered region is covered with a plastic sleeve.

10 Claims, 3 Drawing Sheets

GUIDEWIRE WITH SPRING AND A HEAT SHRINKABLE CONNECTION

FIELD OF THE INVENTION

The present invention relates to guidewires, and more specifically, to a guidewire having a radiopaque distal end.

BACKGROUND ART

Percutaneous angioplasty is a therapeutic medical procedure that can increase blood flow through a blood vessel. It can sometimes be used as an alternative to coronary by-pass surgery for example. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

A known technique for positioning the balloon catheter uses an elongated guidewire that is inserted into the patient and routed through the cardiovascular system as guidewire progress is viewed on an x-ray imaging screen.

Representative prior art patents that disclose flexible, elongated guidewires are U.S. Pat. No. 4,545,390 to Leary, U.S. Pat. No. 4,538,622 to Samson et al. and U.S. Pat. No. 3,906,938 to Fleischhacker and U.S. Pat. No. 4,846,186 to Box et al. The Box et al. patent is incorporated herein by reference.

One problem with currently available guidewires concerns the visibility of the guidewire. If the guidewire is fully opaque on a viewing screen, it can hinder viewing of post angioplasty angiograms used in studying the results produced by the angioplasty, especially in the arterial area proximal to the coil/tip section. Guidewires that have only an opaque tip do not adequately depict the arterial path on the viewing monitor.

U.S. Pat. No. 4,922,924 to Gambale et al. concerns a guidewire for use in placing a catheter. The guidewire includes a coil assembly that is formed from a highly radiopaque coil and a non-radiopaque coil, arranged in bifilar arrangement to define a moderate radiopacity guidewire section.

DISCLOSURE OF THE INVENTION

A guidewire constructed in accordance with the invention includes an elongated core wire including a flexible reduced diameter distal end and a spring made up of multiple coils of wire wound to form a first, generally uniform diameter spring portion and a spring portion having smaller diameter coils that engage the core wire. A plastic sleeve engages the reduced coil diameter portion of the spring and overlies at least some of the smaller diameter coils of the spring.

The spring is constructed of a radiopaque material so that the tip of the guidewire is radiopaque when viewed on a fluoroscope or an x-ray. Most preferably, only a short segment of the guidewire (approximately 3 cm) is radiopaque so that the physician's view of the subject just proximal of the guidewire tip is not impeded.

In accordance with a preferred design, the spring is welded or soldered to the guidewire's distal tip. The plastic sleeve holds the spring to the core wire at a proximal end of the spring. The core wire is preferably flattened at its distalmost tip and this flattened portion allows the distal end of the guidewire to be easily shaped and prevents the spring or coil from separating from the guidewire in the event the distal tip weld should fail.

The use of a plastic sleeve to overlie or cover a small portion of the spring serves as a mechanical bond between the proximal end of the spring and the core wire. Additionally, the plastic sleeve provides a relatively smooth transition from the uniform diameter of the core wire to the outer diameter of the spring or coil.

In an alternative embodiment, a plurality of highly radiopaque marker bands are spaced from each other along a segment of the core wire proximal to the reduced coil diameter portion of the spring. The bands are under the sleeve and are thereby held in place. The marker bands aid an attending physician in monitoring the position of the guidewire.

These and other objects, advantages and features of the invention will become better understood from the following detailed description that describes a preferred embodiment of the invention in conjunction with the accompanying drawings.

BEST MODE FOR CARRYING OUT THE INVENTION

Figures 1, 3:
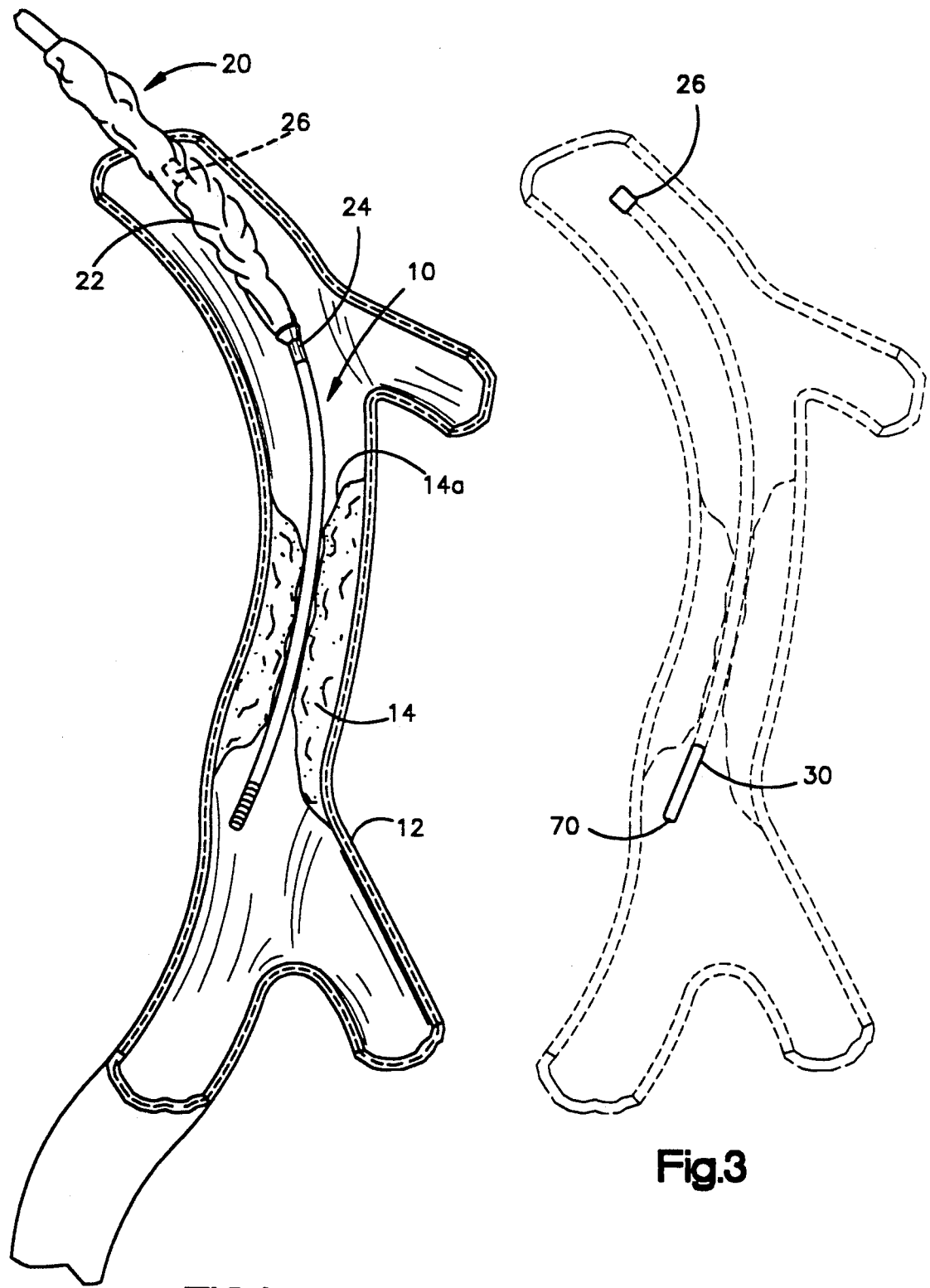
FIG. 1 is a diagrammatic view showing a blood vessel that has been occluded with deposits along an inner wall and shows the positioning of a flexible guidewire within the blood vessel.
FIG. 3 is a view of a flexible guidewire constructed in accordance with the invention as it appears when viewed on a fluoroscopic examining screen.

Turning now to the drawings, FIG. 1 illustrates a distal portion of a flexible, small diameter guidewire 10 that can be guided through a patient cardiovascular system. A distal end of the guidewire is shown in FIG. 1 bridging a region in a blood vessel 12 having occlusions 14 that restrict blood flow through the blood vessel 12. The guidewire 10 is long enough to be routed from a patient entry point through the patient to the obstructed blood vessel region. In a preferred embodiment the guidewire has a length of 175 cm. (approximately 69 inches). As the guidewire 10 is inserted along a tortuous path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a passageway or lumen that extends from a proximal location outside the patient to a distally located balloon 22. Fluid is routed into the catheter through this lumen to inflate the balloon 22. The catheter 20 includes a marker band 26 that is attached to a small tube (not shown) that places the band 26 under the balloon 22 approximately in the middle of the balloon to aid the attending physician in monitoring balloon catheter progress as the catheter is positioned within the patient. A second, center passageway or lumen in the catheter 20 has a diameter sufficient to accommodate the guidewire 10 so that the catheter 20 can be slid back and forth over the guidewire.

An extreme distal tip 30 of the guidewire 10 is flexible and can be bent to a predetermined configuration to facilitate routing the guidewire 10 along the cardiovascular system to the FIG. 1 region of the blood vessel 12. The pre-bent tip can be re-oriented by the physician. Torques applied to the proximal end of the guidewire are transmitted along the length of the guidewire and re-orient the distal tip to point in a desired direction. On the viewing screen, the distal tip portion 30 is visible to the attending physician to facilitate manipulation of the guidewire.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

Figure 2:
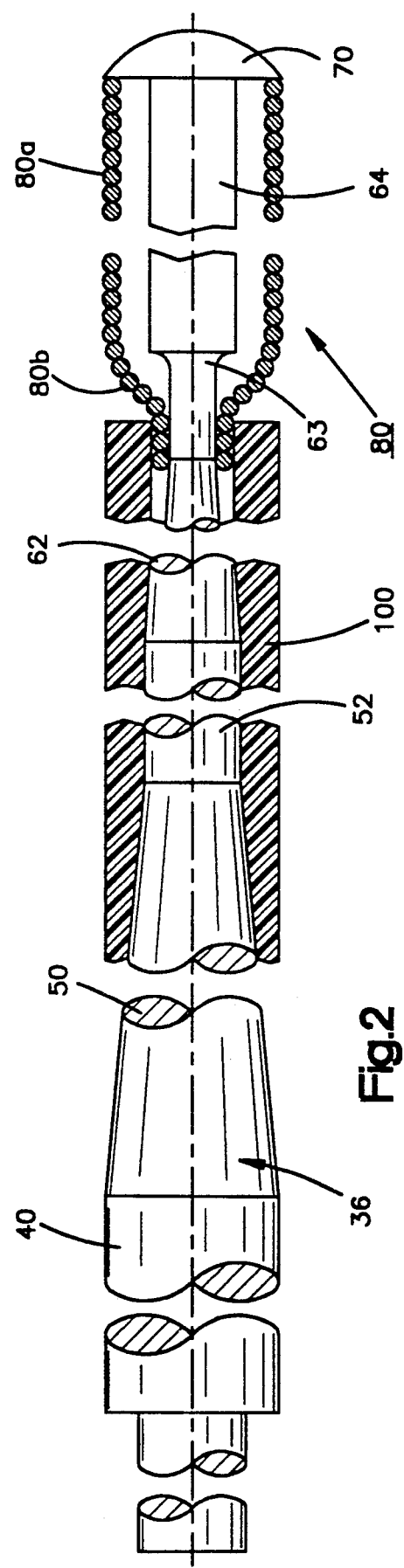
FIG. 2 is an elevation segmented view of a flexible guidewire constructed in accordance with the invention.

Turning now to FIG. 2, the guidewire 10 is seen to include a center metallic wire core 36 having a first or proximal uniform diameter portion 40 with a diameter D, in the range 0.009–0.038 inch, extending well over half the length of the guidewire. To improve the depiction of details of the distal portion of the guidewire 10, this uniform diameter elongated portion 40 has been sectioned and a major portion of its length deleted from FIG. 2.

The total length of the uniform diameter portion 40 is approximately 148 cm. of the total guidewire length of 175 cm. It is typically covered with a suitable coating to make its outer surface lubricous.

At the guidewire's distal end, the wire core 36 tapers along a segment 50 uniformly to a segment 52 having a uniform diameter D'. The core wire 36 again tapers uniformly along a segment 62 to a distal end 63 of the core wire.

At its distal end 63, the core wire 36 has a flattened tip portion 64. A weld 70 or other means of attachment such as soldering or brazing attaches a spring 80 to the flattened portion of the core wire 36. The weld, braze or solder 70 defines a smooth hemispherical bead that does not damage the inner lining of the blood vessels as the guidewire tip comes in contact with those linings.

The spring 80 includes a closely packed uniform diameter segment 80a with adjacent coils separated by a spacing or pitch distance of between 0.0005 and 0.002 inches and an optimum or preferred spacing of 0.001 inch. A tapered spring segment 80b overlies the core wire near a proximal end of the flattened portion 64. The diameter of the spring 80 tapers from a diameter at 80b that is equal to the core wire portion 40 (0.009–0.038 inch) to a diameter at 80b that is slightly smaller than the width of the flattened portion 64 of the core wire. A preferred spring is formed of coiled platinum wire having a wire diameter of 0.002 to 0.003 inches. The platinum wire is radiopaque and therefore the spring 80 forms the visible band 30 that is visible in the FIG. 3 depiction.

The small diameter coils of the spring section having a reduced diameter 80b are covered with a plastic such as a polymer sleeve 100 constructed from polytetrafluoroethylene. This can be accomplished by heat shrinking the sleeve 100 onto the spring 80. The covering sleeve 100 bonds the spring 80 and core wire 36 together and provides a consistent diameter between the core wire portion 40 and the spring 80.

The guidewire 10 depicted in FIG. 2 is particularly suited for insertion into small diameter blood vessels and can be used, for example, for positioning a balloon in a bridging relationship within the coronary artery.

FIG. 3 illustrates the image of the guidewire 10 that a physician would see while using the guidewire during angioplasty. Unlike a fully radiopaque guidewire, the visible band 30 is limited to the distal 3 centimeters of the guidewire tip defined by the radiopaque spring 80.

The core 36 is constructed from a uniform diameter metallic wire that is centerless ground along the tapered segment 50 to the reduced diameter segment 52 and again ground along the tapered segment 62. The distal end 64 of the core wire 36 is flattened by rolling or stamping to increase the flexibility of the guidewire's tip. The core wire's flattened portion has a greater width than the diameter of the tapered spring portion 80b and thus prevents the spring 80 from separating if the weld 70 fails.

Figure 4:
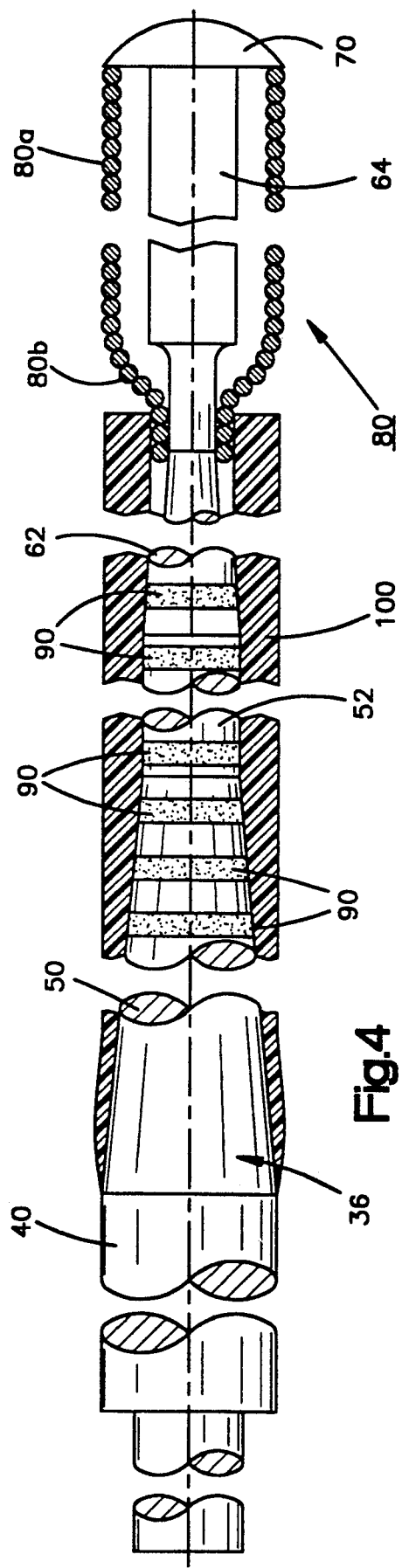
FIG. 4 is an elevation segmented view of an alternative embodiment of a flexible guidewire constructed in accordance with the invention.

FIG. 4 illustrates an alternative embodiment of the guidewire 10. A plurality of highly radiopaque marker bands 90 are spaced from each other along the core wire 36 proximal to the tapered spring segment 80b. The marker bands 90 are placed under the sleeve 100. The sleeve 100 is made an appropriate length to cover all the bands 90 and thereby hold them in place.

There are between three and nine marker bands 90 placed between one and three centimeters apart. The bands can, therefore, be placed such that they are spaced along virtually all of the tapering portions of the core wire 36.

The marker bands 90 are preferably platinum rings that are commercially available. The rings are placed over the core wire 36 prior to covering the spring coils 80b and the bands with the sleeve 100.

The dimensions mentioned in this specification are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

We claim:

1. A guidewire comprising:
a) an elongated core wire including a first uniform diameter portion and a second more flexible reduced diameter portion, the reduced diameter portion extending to a distal end of said guidewire;
b) a coiled spring having multiple coils of wire wound to a first, generally uniform diameter along a distal end of said coiled spring, the uniform diameter coils surrounding a distal end of the flexible reduced diameter portion of the elongated core wire and further having multiple reduced diameter coils that taper in diameter to a coiled spring segment at a proximal end of the coiled spring where the coiled spring terminates and engages the flexible reduced diameter portion of said core wire; and
c) a sleeve overlying a section of the reduced diameter portion of the core wire including at least some of the reduced diameter coils to bond the proximal end of the coiled spring to the reduced diameter portion of the core wire and to provide a more consistent guidewire outer diameter over the section of the core wire overlying the sleeve.

2. The guidewire of claim 1 wherein the elongated core wire includes a flattened portion at the distal end of the reduced diameter portion at least partially surrounded by the uniform diameter spring coils, the flattened portion being wider than at least some of the reduced diameter coils engaging the reduced diameter portion of the core wire.

3. The guidewire of claim 1 wherein the spring is constructed of a radiopaque metal wire.

4. A guidewire comprising:
   a) an elongated core wire including a flexible, reduced diameter, distal portion and a large diameter proximal portion;
   b) a coiled-wire, highly radiopaque spring having distal and proximal ends engaging the core wire and including a first region extending from the distal end of the spring made up of coils having a generally uniform diameter and a second region made up of coils having a lesser diameter which taper in diameter to a proximal end of the spring where the spring terminates and engages the reduced diameter distal portion of the core wire;
   c) connection means for attaching the distal and proximal ends of the coiled wire spring to the core wire at spaced apart locations comprising:
      i) a distal hemispherical connector connecting a distal end of the spring to a distal end of the core wire; and
      ii) a heat shrinkable plastic sleeve overlying a section of the reduced diameter portion of the core wire including at least some of the lesser diameter coils which when shrunk through an application of heat bonds the proximal end of the spring where the spring terminates to the reduced diameter portion of the core wire and provides a more consistent guidewire outer diameter along a section of the reduced diameter, distal portion of the elongated core wire.

5. The guidewire of claim 4 wherein the distal portion of the core wire includes a flattened portion that is surrounded by the spring and where a width of the flattened portion is greater than at least some of the reduced diameter coils of the tapered region of said spring.

6. A guidewire comprising:
   a) an elongated core wire including a flexible distal portion having a reduced diameter and a large diameter proximal portion;
   b) a coiled spring having a proximal and a distal end and having multiple coils of wire extending from the distal end of the spring wound to a first, generally uniform diameter surrounding the flexible distal portion of the core wire and further having multiple reduced diameter coils that taper in diameter to at least one coiled spring segment terminating at the proximal end of the spring that engages the flexible distal portion of said core wire;
   c) connection means for attaching the distal and proximal ends of the coiled wire spring to the core wire at spaced apart locations; and
   d) the distal portion of the core wire including a flattened portion that is surrounded by the spring and wherein a width of the flattened portion is greater than at least some of the lesser diameter coils of the tapered portion of said spring;
   e) the connection means comprising a cover layer of a heat shrinkable plastic engaging a section of the reduced diameter portion of the core wire including at least some of the lesser diameter coils of the coiled wire spring and having been shrunk through an application of heat, the shrunken plastic cover layer bonding the proximal end of the spring to the reduced diameter portion of the core wire and providing a more consistent guidewire outer diameter over the distal portion of the core wire engaged by the cover layer and further comprising a guidewire distal tip that joins the distal end of the spring to the core wire.

7. A guidewire comprising:
   a) an elongated core wire including a flexible distal portion having a reduced diameter and a large diameter proximal portion;
   b) a coiled spring having a proximal and a distal end and having multiple coils of highly radiopaque metal wire extending from the distal end of the coiled spring and wound to a first, generally uniform diameter surrounding the flexible distal portion of the core wire and further having multiple reduced diameter coils that taper in diameter to at least one coiled spring segment terminating at the proximal end of the coiled spring that engages the flexible distal portion of said core wire;
   c) a plurality of highly radiopaque marker bands spaced from each other along the reduced diameter portion of said core wire proximal to the region the reduced diameter coils of the spring engages the flexible, distal portion of the core wire; and
   d) a sleeve overlying a section of the reduced diameter portion of the core wire including at least some of the reduced diameter coils to bond the proximal end of the coiled spring to the reduced diameter portion of the core wire and to provide a more consistent guidewire outer diameter over the section of the core wire engaged by the sleeve.

8. The guidewire of claim 7 wherein the distal portion of the elongated core wire comprises a flattened portion at least partially surrounded by the uniform diameter spring coils and where a width of the flattened section is greater than at least some of the reduced diameter coils.

9. The guidewire of claim 7 wherein the sleeve overlies at least some of the marker bands.

10. The guidewire of claim 7 where the marker bands comprise platinum metal bands.

* * * * *